United States Patent
Kuo

(10) Patent No.: US 8,111,019 B2
(45) Date of Patent: Feb. 7, 2012

(54) SENSING TYPE CONTROL CIRCUIT FOR ELECTRONIC APPARATUS

(75) Inventor: Fu-Rung Kuo, Taipei (TW)

(73) Assignee: Princeton Technology Corporation, Taipei County (TW)

( * ) Notice: Subject to any disclaimer, the term of this patent is extended or adjusted under 35 U.S.C. 154(b) by 421 days.

(21) Appl. No.: 12/491,589

(22) Filed: Jun. 25, 2009

(65) Prior Publication Data

US 2010/0164407 A1 Jul. 1, 2010

(30) Foreign Application Priority Data

Dec. 31, 2008 (TW) .............................. 97223948 U

(51) Int. Cl.
*H05B 37/02* (2006.01)

(52) U.S. Cl. ....................................... 315/308; 315/291

(58) Field of Classification Search ............... 315/200 R, 315/246, 272, 291, 307, 308, 309
See application file for complete search history.

(56) References Cited

U.S. PATENT DOCUMENTS

| | | | | |
|---|---|---|---|---|
| 6,087,787 A | * | 7/2000 | Williams | 315/307 |
| 7,894,218 B2 | * | 2/2011 | Feldtkeller et al. | 363/45 |
| 2008/0205104 A1 | * | 8/2008 | Lev et al. | 363/98 |

* cited by examiner

*Primary Examiner* — Don Le

(74) *Attorney, Agent, or Firm* — Muncy, Geissler, Olds & Lowe, PLLC

(57) ABSTRACT

A sensing type control circuit for an electronic apparatus is provided. An output unit is coupled between an external power source and the electronic apparatus and provides varied power supply to the electronic apparatus according to a control signal. A switch is coupled between the external power source and the output unit and disconnects or connects the external power source. A control unit receives a sensing signal and generates the control signal to the output unit according to the received signal. A sensing unit includes a sensing device and senses an external variation, wherein the sensing unit generates the sensing signal to the control unit when the sensing device senses an excitation.

7 Claims, 4 Drawing Sheets

SENSING TYPE CONTROL CIRCUIT FOR ELECTRONIC APPARATUS

CROSS REFERENCE TO RELATED APPLICATIONS

This Application claims priority of Taiwan Patent Application No. 097223948, filed on Dec. 31, 2008, the entirety of which is incorporated by reference herein.

BACKGROUND OF THE INVENTION

1. Field of the Invention

The invention relates to a control circuit, and more particularly to a control circuit comprising a sensing device for an electronic apparatus.

2. Description of the Related Art

Electronic apparatuses, such as lamps, fans and so on, do not need complex manipulation. Therefore, a simple switch and a control integrate circuit (IC) are used to control the electronic apparatuses in order to simplify structure and increase manipulate conveniently. The switch is used as a single input terminal that can provide external control which may be varied to provide various operation models according to switching number of the switch correspondingly.

However, with one switch, constant switching damages and wears the switch over time. Therefore, a control circuit for an additional input terminal for an electronic apparatus that can provide external control thereto which may be varied, is desired.

BRIEF SUMMARY OF THE INVENTION

A sensing type control circuit for an electronic apparatus is provided. A sensing device is disposed to add another input terminal to an electronic apparatus, providing external control thereto which may be varied, thus decreasing damage and wear to a single switch which is used as an input terminal.

An exemplary embodiment of a sensing type control circuit for an electronic apparatus is provided. The sensing type control circuit comprises: an output unit coupled between an external power source and the electronic apparatus, providing varied power supply to the electronic apparatus according to a control signal; a switch coupled between the external power source and the output unit, disconnecting or connecting the external power source; a control unit, receiving a sensing signal and generating the control signal to the output unit according to the received signal; and a sensing unit, comprising a sensing device, sensing an external variation, wherein the sensing unit generates the sensing signal to the control unit when the sensing device senses an excitation.

The sensing type control circuit of the invention decreases damage and wear to switches of electronic apparatuses. In the invention, the sensing device functions as an additional input terminal, such that two control operations "switching" and "powering on/off" are controlled by different input terminals. Thus, decreasing damage and wear to switches of electronic apparatuses and increasing operating lifespan. Furthermore, the sensing device may be integrated into an original control IC due to its small size, thus simplifying design applications.

A detailed description is given in the following embodiments with reference to the accompanying drawings.

BRIEF DESCRIPTION OF DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
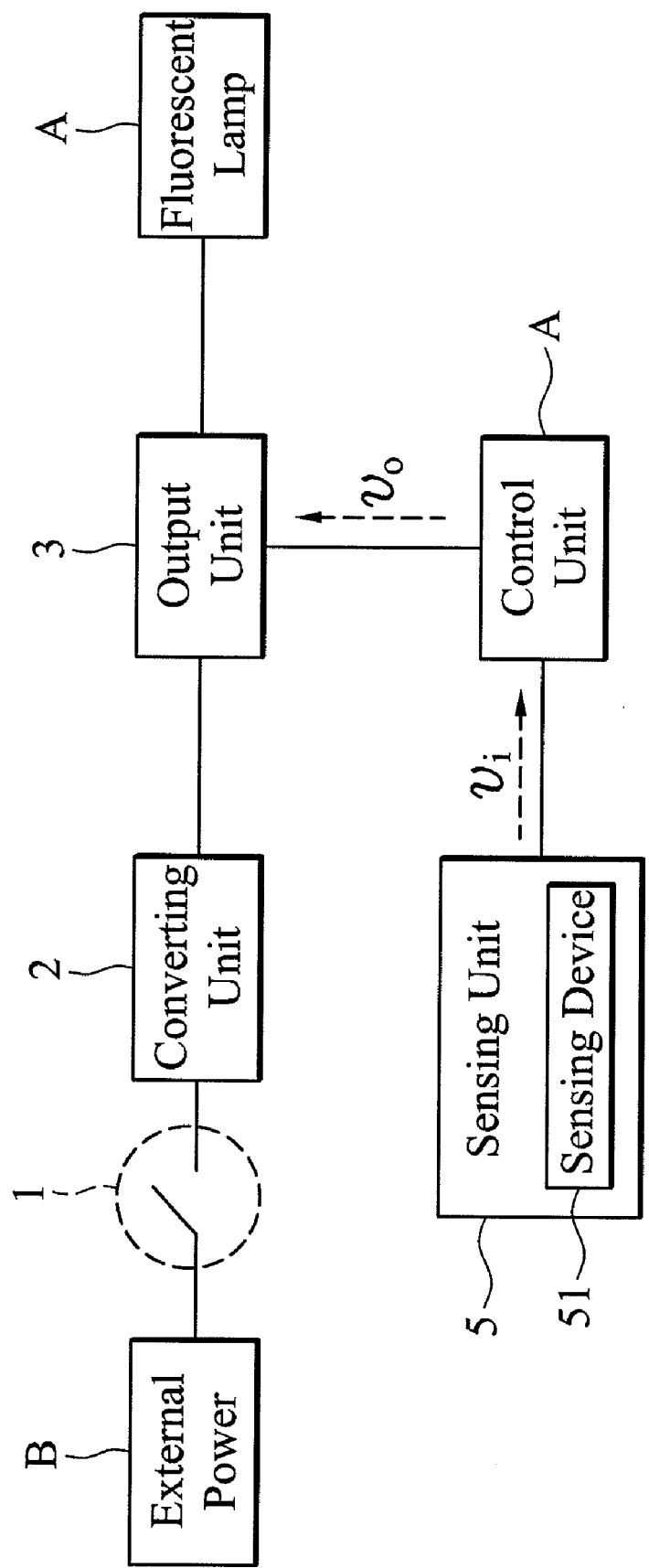
FIG. 1 shows a block diagram of a sensing type control circuit according to an embodiment of the invention.
Figure 2:
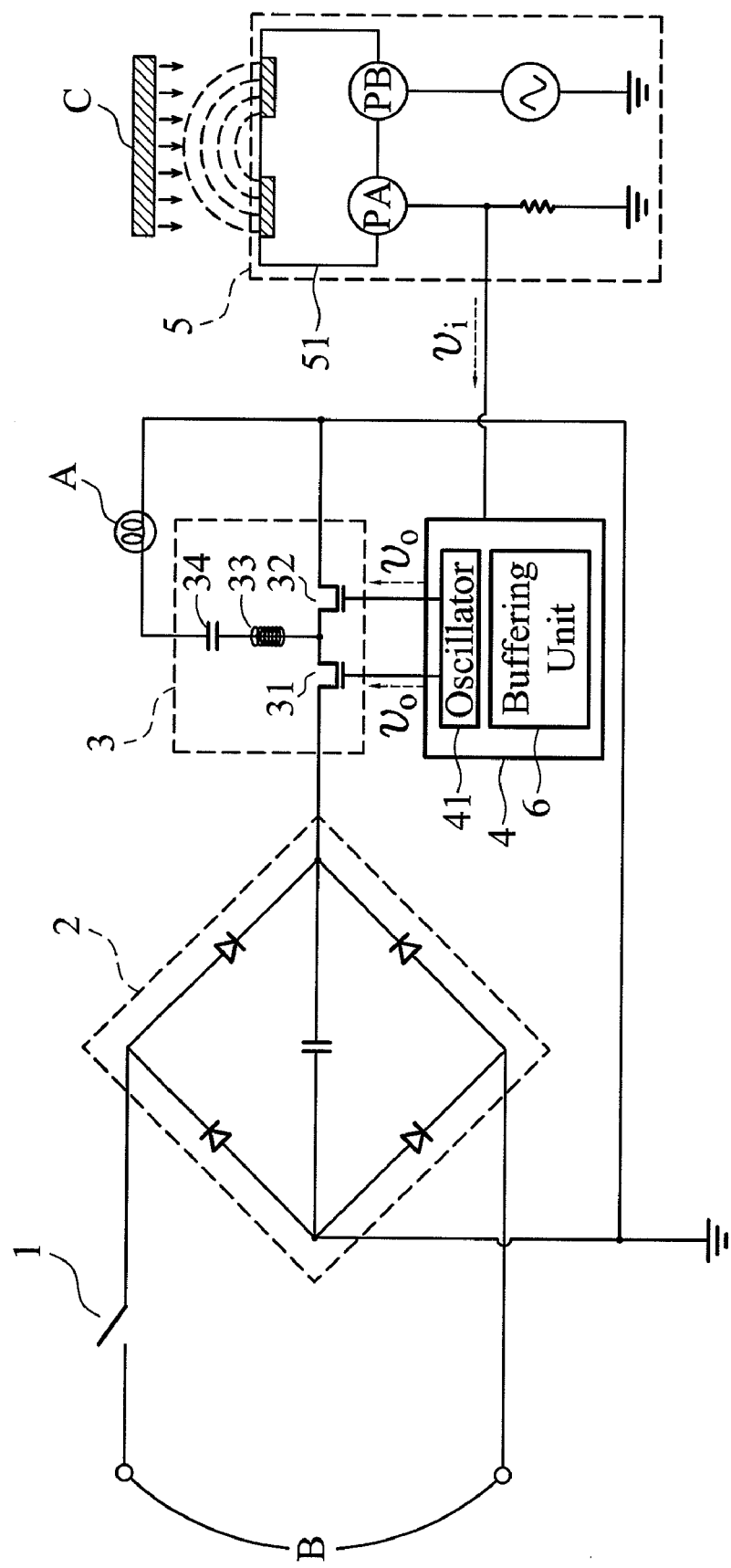
FIG. 2 shows a schematic diagram of a sensing type control circuit according to an embodiment of the invention.
Figure 3:
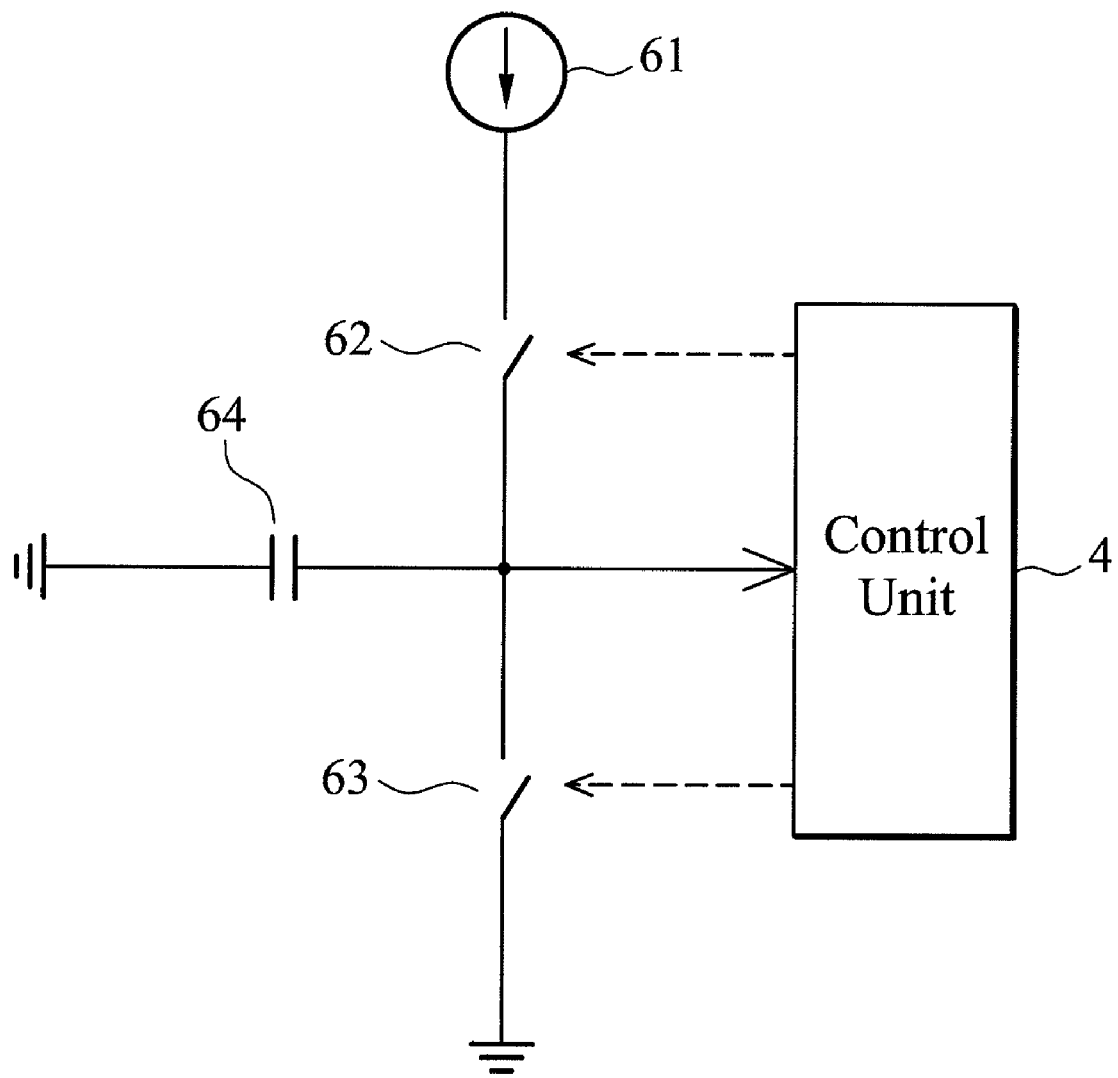
FIG. 3 shows a schematic diagram of a buffing circuit according to an embodiment of the invention.

FIG. 1 to FIG. 3 show a sensing type control circuit for controlling a fluorescent lamp A according to an embodiment of the invention, wherein a power supplied to the fluorescent lamp A is a direct current (DC) power and an external power source B is a alternating current (AC) power. The sensing type control circuit comprises a switch 1, a converting unit 2, an output unit 3, a control unit 4 and a sensing unit 5. The switch 1 is disposed between the external power source B and the converting unit 2, and is used to disconnect or connect the external power source B. The converting unit 2 is disposed between the switch 1 and the output unit 3. When a power supplied to the fluorescent lamp A (i.e. an electronic apparatus) is a DC power and the external power source B is an AC power, the converting unit 2 converts the AC power into the DC power for the fluorescent lamp A. The converting unit 2 is a standard rectifying and filtering circuit comprising a bridge rectifier and a capacitor.

The output unit 3 is coupled between the converting unit 2 and the fluorescent lamp A, and provides varied power supply to the fluorescent lamp A according to a control signal $v_O$ generated by the control unit 4. The output unit 3 comprises a first NMOS transistor 31, a second NMOS transistor 32, an inductor 33 and a capacitor 34. A drain of the first NMOS transistor 31 is coupled to the converting unit 2 to receive the DC power converted by the converting unit 2. A gate of the first NMOS transistor 31 is coupled to the control unit 4 to receive the control signal $v_O$. A drain of the second NMOS transistor 32 is coupled to a source of the first NMOS transistor 31. A gate of the second NMOS transistor 32 is coupled to the control unit 4 to receive the control signal $v_O$. A source of the second NMOS transistor 32 is coupled to a virtual ground terminal. One end of the inductor 33 is coupled between the source of the first NMOS transistor 31 and the drain of the second NMOS transistor 32, and another end of the inductor 33 is coupled to one end of the capacitor 34. Another end of the capacitor 34 is coupled to the fluorescent lamp A.

The control unit 4 receives a sensing signal $v_i$ and provides the control signal $v_O$ corresponding to the received sensing signal $v_i$ to the output unit 3. The control unit 4 comprises a buffering unit 6 which is used to buffer the received signal to hold a time period t and provide the control signal $v_O$ to the output unit 3 after the time period t has been reached. The buffering unit 6 comprises a micro-current source 61, two switches 62 and 63 and a capacitor 64. The two switches 62 and 63 are connected in series, wherein one end of the switches connected in series is coupled to the micro-current source 61 and another end is coupled to a ground terminal. One end of the capacitor 64 is coupled between the switches 62 and 63 and another end of the capacitor 64 is coupled to the ground terminal. The micro-current source 61 may provide a stable micro-current. The control unit 4 controls the switches 62 and 63 to turn on or off according to the received signal, so as to control whether the capacitor 64 is charged by the micro-current source 61. The buffering time period t is a time that the micro-current source 61 has finished charging the capacitor 64. In addition, the control unit 4 further comprises an oscillator 41. The control unit 4 changes a frequency of the oscillator 41 to output a current with various values to the output unit 3. Therefore, the control signal $v_O$ transmitted from the control unit 4 to the output unit 3 is the current.

The sensing unit 5 comprises a sensing device 51 for sensing an external variation. When the sensing device 51 senses an excitation, the sensing unit 5 may generate the sensing signal $v_i$ and provide the sensing signal $v_i$ to the control unit 4. In the embodiment, the sensing device 51 is a capacitor type object sensor comprising a capacitor which is composed of two flat plates PA and PB, wherein a dielectric material is disposed between the flat plates PA and PB. A current is flowed therethrough when a signal is coupled from the flat plate PA to PB. If no object C approaches to a sensing area formed by the flat plates PA and PB, the coupling value is very small. If the object C appears in the sensing area, capacitance of the capacitor may be changed to vary the coupling value (i.e. the sensing device 51 senses an external variation).

A control method for a sensing type control circuit according to an embodiment of the invention is provided. First, a switch is turned on to connect an external power source. Next, a power is provided to a converting unit, and the converting unit converts the power from AC to DC and provides the DC power to an output unit. Next, a control unit delays a time period t to generate and output a control signal to the output unit. Next, the output unit generates a current with a first value to a fluorescent lamp according to the control signal generated by the control unit. Next, the fluorescent lamp is lighted at a first brightness. Next, when a sensing device senses an excitation, a sensing unit may generate and transmit a sensing signal to the control unit. Next, the control unit delays a time period t to generate and output another control signal to the output unit. Next, the output unit generates a current with a second value to the fluorescent lamp according to another control signal generated by the control unit, such that the fluorescent lamp is lighted at a second brightness and so on. When the sensing device 51 senses each excitation, the lighted brightness of the fluorescent lamp is changed to a corresponding brightness. Finally, the switch is turned off. When the sensing device senses an excitation and a delay time t corresponding to the last excitation has not been reached, the control unit stops counting of the delay time t corresponding to the last excitation and starts to count a delay time t corresponding to the current excitation.

Figure 4:
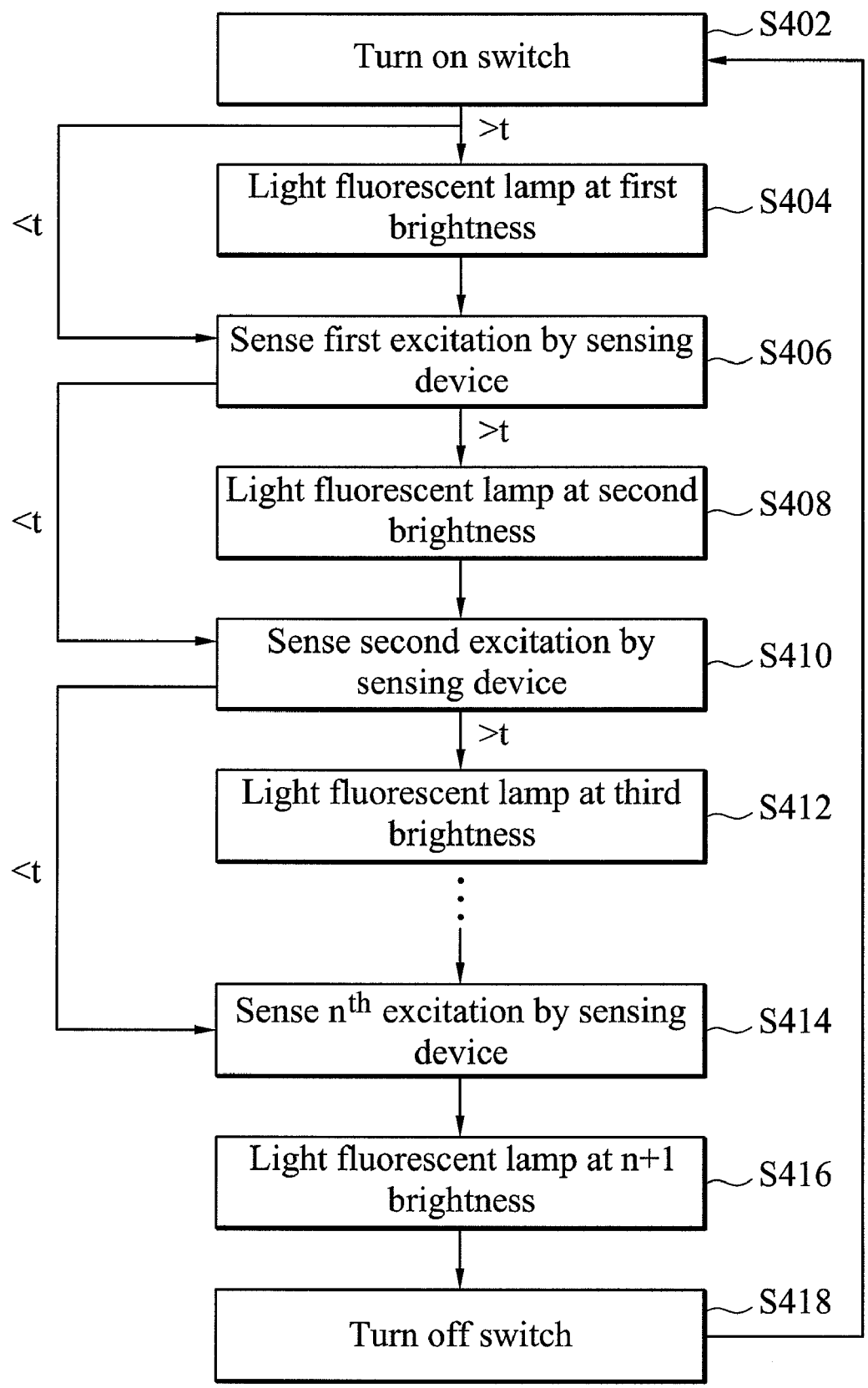
FIG. 4 shows a flowchart illustrating a method for lighting a fluorescent lamp by a sensing type control circuit according to an embodiment of the invention.

Referring to FIG. 4, FIG. 4 shows a method for lighting a fluorescent lamp by a sensing type control circuit according to an embodiment of the invention. First, in step S402, a switch is turned on. Next, after delaying a first time t, the fluorescent lamp is lighted at a first brightness (step S404). Next, a sensing device senses a first excitation (step S406), such as a user may use his hand to approach a sensing device, so as to activate the sensing device. The sensing device may be a capacitor type object sensor that is produced as a switch model. Next, after delaying a second time t, the fluorescent lamp is lighted at a second brightness (step S408). Next, the sensing device senses a second excitation (step S410). Next, after delaying a third time t, the fluorescent lamp is lighted at a third brightness (step S412) and so on (steps S414 and S416) until the switch is turned off (step S418). When the sensing device senses an excitation and a delay time t corresponding to the last excitation has not been reached, counting of the delay time t corresponding to the last excitation is stopped and counting of a delay time t corresponding to the current excitation is started. The fluorescent lamp is lighted at a brightness corresponding to the current excitation when no next excitation is sensed before the delay time t corresponding to the current excitation has been reached.

Therefore, the sensing type control circuit of the invention decreases damage and wear to switches of electronic apparatuses. In the invention, the sensing device functions as an additional input terminal, such that two control operations "switching" and "powering on/off" are controlled by different input terminals, thus decreasing damage and wear to switches of electronic apparatuses and increasing operating lifespan. Furthermore, the sensing device may be integrated into an original control IC due to its small size, thus simplifying design applications. In addition, when turning on or off the fluorescent lamp, the charging buffer time may avoid flickering of the fluorescent lamp. Simultaneously, power is saved and operating lifespan of the fluorescent lamp is increased.

While the invention has been described by way of example and in terms of preferred embodiment, it is to be understood that the invention is not limited thereto. Those who are skilled in this technology can still make various alterations and modifications without departing from the scope and spirit of this invention. Therefore, the scope of the present invention shall be defined and protected by the following claims and their equivalents.

What is claimed is:

1. A sensing type control circuit for an electronic apparatus, comprising:
   an output unit coupled between an external power source and the electronic apparatus, providing varied power supply to the electronic apparatus according to a control signal;
   a switch coupled between the external power source and the output unit, disconnecting or connecting the external power source;
   a control unit, receiving a sensing signal and generating the control signal to the output unit according to the received signal, wherein the control unit comprises:
      a buffering unit for buffering the received signal until a specific time period has been reached and transmitting the control signal to the output unit when the specific time period has been reached, wherein the buffering unit comprises:
         a micro-current source providing a stable micro-current;
         two switches connected in series, wherein one end of the switches connected in series is coupled to the micro-current source and another end is coupled to a ground terminal; and
         a capacitor, wherein the control unit controls the switches to charge the capacitor according to the received signal, and the specific time period is a time that the micro-current source has finished charging the capacitor; and
   a sensing unit, comprising a sensing device, sensing an external variation, wherein the sensing unit generates the sensing signal to the control unit when the sensing device senses an excitation.

2. The sensing type control circuit as claimed in claim 1, further comprising:
   a converting unit coupled between the switch and the output unit, wherein when a power supplied to the electronic apparatus is a DC power and the external power source is an AC power, the converting unit converts the AC power into the DC power for the electronic apparatus.

3. The sensing type control circuit as claimed in claim 2, wherein the converting unit is a standard rectifying and filtering circuit comprising a bridge rectifier and a capacitor.

4. The sensing type control circuit as claimed in claim 3, wherein the control unit further comprises an oscillator, and the control unit changes a frequency of the oscillator to output a current with various values to the output unit, wherein the control signal transmitted from the control unit to the output unit is the current.

5. The sensing type control circuit as claimed in claim 4, wherein the output unit comprises:
   a first NMOS transistor comprising a drain coupled to the converting unit for receiving the DC power and a gate coupled to the control unit for receiving the control signal;
   a second NMOS transistor comprising a drain coupled to a source of the first NMOS transistor, a gate coupled to the control unit for receiving the control signal and a source coupled to a virtual ground terminal;
   an inductor, wherein one end of the inductor is coupled between the source of the first NMOS transistor and the drain of the second NMOS transistor; and
   a capacitor coupled between the electronic apparatus and another end of the inductor.

6. The sensing type control circuit as claimed in claim 5, wherein the electronic apparatus is a fluorescent lamp.

7. The sensing type control circuit as claimed in claim 1, wherein the sensing device is a capacitor type object sensor.

\* \* \* \* \*